United States Patent
Sun et al.

(10) Patent No.: US 7,916,831 B2
(45) Date of Patent: Mar. 29, 2011

(54) X-RAY DETECTOR AND X-RAY CT APPARATUS

(75) Inventors: Yunfeng Sun, Shanghai (CN); Jiaqin Dong, Beijing (CN); Jianying Li, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 211 days.

(21) Appl. No.: 12/433,494

(22) Filed: Apr. 30, 2009

(65) Prior Publication Data

US 2009/0274266 A1 Nov. 5, 2009

(30) Foreign Application Priority Data

Apr. 30, 2008 (CN) .......................... 2008 1 0094969

(51) Int. Cl.
*A61B 6/00* (2006.01)
(52) U.S. Cl. ...................... 378/19; 378/98.8; 250/370.09
(58) Field of Classification Search .................... 378/19, 378/98.8; 250/370.08, 370.09
See application file for complete search history.

(56) References Cited

U.S. PATENT DOCUMENTS

| | | | |
|---|---|---|---|
| 4,926,052 A | 5/1990 | Hatayama et al. | 250/370.14 |
| 5,262,871 A | 11/1993 | Wilder et al. | 348/307 |
| 5,400,378 A | 3/1995 | Toth | 378/16 |
| 6,255,708 B1 | 7/2001 | Sudharsanan et al. | 257/428 |
| 6,775,352 B2 | 8/2004 | Toth et al. | 378/108 |
| 6,836,529 B2 | 12/2004 | Li et al. | 378/8 |
| 7,260,174 B2 | 8/2007 | Hoffman et al. | 378/19 |
| 7,274,768 B2 | 9/2007 | Green | 378/57 |
| 2001/0004548 A1 | 6/2001 | French | 438/585 |
| 2003/0035510 A1 | 2/2003 | Strommer | 378/98.8 |
| 2004/0032928 A1 | 2/2004 | Toth et al. | 378/108 |
| 2005/0253079 A1 | 11/2005 | Hoffman | 250/370.13 |
| 2006/0056581 A1 | 3/2006 | Hoffman et al. | 378/19 |
| 2008/0230709 A1 | 9/2008 | Tkaczyk et al. | 250/370.09 |

*Primary Examiner* — Courtney Thomas
(74) *Attorney, Agent, or Firm* — Armstrong Teasdale LLP

(57) ABSTRACT

An X-ray detector includes a single-layered semiconductor substrate having an array of detection cells which directly convert photons of X-rays into electrical signals; a first data collecting device which collects data with respect to the array of detection cells in a photon counting mode; and a second data collecting device which collects data with respect to the array of detection cells in a current measuring mode.

20 Claims, 18 Drawing Sheets

X-RAY DETECTOR AND X-RAY CT APPARATUS

CROSS REFERENCE TO RELATED APPLICATIONS

This application claims the benefit of Chinese Patent Application No. 200810094969.4 filed Apr. 30, 2008, which is hereby incorporated by reference in its entirety.

BACKGROUND OF THE INVENTION

The embodiments described herein relate to an X-ray detector and an X-ray CT (computed tomography) apparatus, and more particularly to an X-ray detector using a semiconductor which directly converts photons of X-rays into electrical signals and an X-ray CT apparatus having such an X-ray detector.

In an X-ray CT apparatus, an X-ray source and an X-ray detector opposite to each other scan a subject to collect projected data, and reconstructs an image on the basis of the projected data. Some X-ray CT apparatuses perform imaging targeted on a specific element by utilizing the difference among elements in the energy-dependence of the X-ray absorption coefficient.

Such an X-ray CT apparatus uses an X-ray detector which counts the photons of X-rays energy by energy. In such an X-ray detector, a semiconductor directly converts photons of X-rays into electrical signals. As the semiconductor, CZT (cadmium zinc telluride) or the like may be used for instance.

In an X-ray detector using such a semiconductor, as the photon count becomes saturated when the flux rate of X-rays becomes high, multiple detecting layers are provided to raise the saturation limit (see U.S. Patent Application No. 2006/0056581 for instance).

Since the saturation limit of photon count is determined by the thickness of each layer in an X-ray detector having multiple semiconductor layers, the manufacture of such X-ray detectors requires sophisticated manufacturing technology and precision manufacturing equipment. For this reason, such X-ray detectors inevitably cost high.

Accordingly, it is desirable to provide an X-ray detector which is adaptable to low to high flux rates with only one layer of semiconductor and an X-ray CT apparatus having such an X-ray detector.

BRIEF DESCRIPTION OF THE INVENTION

A first aspect provides an X-ray detector using a semiconductor which directly converts photons of X-rays into electrical signals, the X-ray detector comprising: a single-layered semiconductor substrate having an array of detection cells which directly convert photons of X-rays into electrical signals; first data collecting device which collects data with respect to the detection cells in a photon counting mode; and second data collecting device which collects data with respect to the detection cells in a current measuring mode.

A second aspect provides an X-ray detector according to the first aspect, wherein the first and second data collecting device collect data regarding common detection cells.

A third aspect provides an X-ray detector according to the first aspect, wherein the first and second data collecting device collect data regarding different detection cells.

A fourth aspect provides an X-ray detector according to the first aspect, wherein the array of detection cells has a common electrode arranged on one of the front face and the rear face of the semiconductor substrate; and a plurality of individual electrodes arranged on the other of the front face and the rear face of the semiconductor substrate.

A fifth aspect provides an X-ray detector according to the fourth aspect, wherein the plurality of individual electrodes are a mixture of a first group of individual electrodes for the first data collecting device, and a second group of individual electrodes for the second data collecting device.

A sixth aspect provides an X-ray detector according to the fifth aspect, wherein the first group of individual electrodes and the second group of individual electrodes share pixels.

A seventh aspect provides an X-ray detector according to the fifth aspect, wherein the first group of individual electrodes and the second group of individual electrodes do not share pixels.

An eighth aspect provides an X-ray detector according to the fourth aspect, wherein the array of detection cells undergo incidence of X-rays on the common electrode side.

A ninth aspect provides an X-ray detector according to the fourth aspect, wherein the array of detection cells undergo incidence of X-rays on the individual electrode side.

A tenth aspect provides an X-ray detector according to the ninth aspect, wherein the array of detection cells undergo incidence of X-rays on a side face of a semiconductor layer between the individual electrodes and the common electrode.

An eleventh aspect provides an X-ray CT apparatus which collects projected data by scanning an object with X-rays and reconstructs an image on the basis of these projected data, the X-ray CT apparatus comprising a single-layered semiconductor substrate having an array of detection cells which directly convert photons of X-rays into electrical signals; first data collecting device which collects data with respect to the detection cells in a photon counting mode; second data collecting device which collects data with respect to the detection cells in a current measuring mode; and image reconstructing device which reconstructs an image based on the data collected by the first data collecting device and an image based on the data collected by the second data collecting device.

A twelfth aspect provides an X-ray CT apparatus according to the 11th aspect, wherein the first and second data collecting device collect data regarding common detection cells.

A thirteenth aspect provides an X-ray CT apparatus according to the 11th aspect, wherein the first and second data collecting device collect data regarding different detection cells.

A fourteenth aspect provides an X-ray CT apparatus according to the 11th aspect, wherein the array of detection cells has a common electrode arranged on one of the front face and the rear face of the semiconductor substrate; and a plurality of individual electrodes arranged on the other of the front face and the rear face of the semiconductor substrate.

A fifteenth aspect provides an X-ray CT apparatus according to the 14th aspect, wherein the plurality of individual electrodes are a mixture of a first group of individual electrodes for the first data collecting device, and a second group of individual electrodes for the second data collecting device.

A sixteenth aspect provides an X-ray CT apparatus according to the 15th aspect, wherein the first group of individual electrodes and the second group of individual electrodes share pixels.

A seventeenth aspect provides an X-ray CT apparatus according to the 15th aspect, wherein the first group of individual electrodes and the second group of individual electrodes do not share pixels.

An eighteenth aspect provides an X-ray CT apparatus according to the 14th aspect, wherein the array of detection cells undergo incidence of X-rays on the common electrode side.

A nineteenth aspect provides an X-ray CT apparatus according to the 14th aspect, wherein the array of detection cells undergo incidence of X-rays on the individual electrode side.

A twentieth aspect provides an X-ray CT apparatus according to the 19th aspect, wherein the array of detection cells undergo incidence of X-rays on a side face of a semiconductor layer between the individual electrodes and the common electrode.

One embodiment provides an X-ray detector that uses a semiconductor which directly converts photons of X-rays into electrical signals and, since it is provided with a single-layered semiconductor substrate having an array of detection cells which directly convert photons of X-rays into electrical signals; first data collecting device which collects data with respect to the detection cells in a photon counting mode; and second data collecting device which collects data with respect to the detection cells in a current measuring mode, an X-ray detector which is adaptable to low flux rates to high flux rates with a single-layered semiconductor can be realized.

Low flux rates are addressed in the photon counting mode. This makes possible data collection regarding parts where the quantity of X-ray absorption is large. Any flux rate that can be addressed in the photon counting mode can be altered by varying the size of detection cells. High flux rates are addressed in the current measuring mode. Data collection in the current measuring mode can be carried out without saturation even at a high flux rate.

Another embodiment provides an X-ray CT apparatus which collects projected data by scanning an object with X-rays and reconstructs an image on the basis of these projected data and, since it is provided with a single-layered semiconductor substrate having an array of detection cells which directly convert photons of X-rays into electrical signals; first data collecting device which collects data with respect to the detection cells in a photon counting mode; second data collecting device which collects data with respect to the detection cells in a current measuring mode; and image reconstructing device which reconstructs an image based on the data collected by the first data collecting device and an image based on the data collected by the second data collecting device, an X-ray CT apparatus having an X-ray detector which is adaptable to low flux rates to high flux rates with a single-layered semiconductor can be realized.

By addressing low flux rates in the photon counting mode and addressing high flux rates in the current measuring mode, it is possible to address any flux rates consecutively from low rates to high rates. The distribution of a specific element can be visualized in an image according to data collected in the photon counting mode, and the distribution of the X-ray absorption coefficients can be visualized in an image according to data collected in the current measuring mode.

Since the first data collecting device and the second data collecting device collect data regarding common detection cells, data collection can be accomplished in two modes regarding every detection cell.

Since the first data collecting device and the second data collecting device collect data regarding different detection cells, each detection cell can be configured optimally for its data collection mode.

Since the array of detection cells has a plurality of individual electrodes arranged on the other of the front face and the rear face of the semiconductor substrate and a common electrode arranged on the one of the front face and the rear face of the semiconductor substrate, the configuration of the array can be simplified.

Since the plurality of individual electrodes is a mixture of a first group of individual electrodes for the first data collecting device and a second group of individual electrodes for the second data collecting device, the first group of individual electrodes and the second group of individual electrodes can be configured optimally for their respective data collection modes.

Since the first group of individual electrodes and the second group of individual electrodes share pixels, data collection can be accomplished in two modes regarding every pixel.

Since the first group of individual electrodes and the second group of individual electrodes do not share pixels, the first group of individual electrodes and the second group of individual electrodes can be configured optimally for their respective data collection modes.

Since the array of detection cells undergo incidence of X-rays on the common electrode side, it can adapt to the two-dimensional distribution of X-rays.

Since the array of detection cells undergo incidence of X-rays on the individual electrode side, it can adapt to the two-dimensional distribution of X-rays.

Since the array of detection cells undergo incidence of X-rays on a side face of a semiconductor layer between the individual electrodes and the common electrode, it can adapt to the one-dimensional distribution of X-rays.

DETAILED DESCRIPTION OF THE INVENTION

Various embodiments of the invention will be described with reference to drawings. Incidentally, the invention is not limited to the embodiments described herein. A schematic configuration of an X-ray CT apparatus is shown in FIG. 1.

Figure 1:
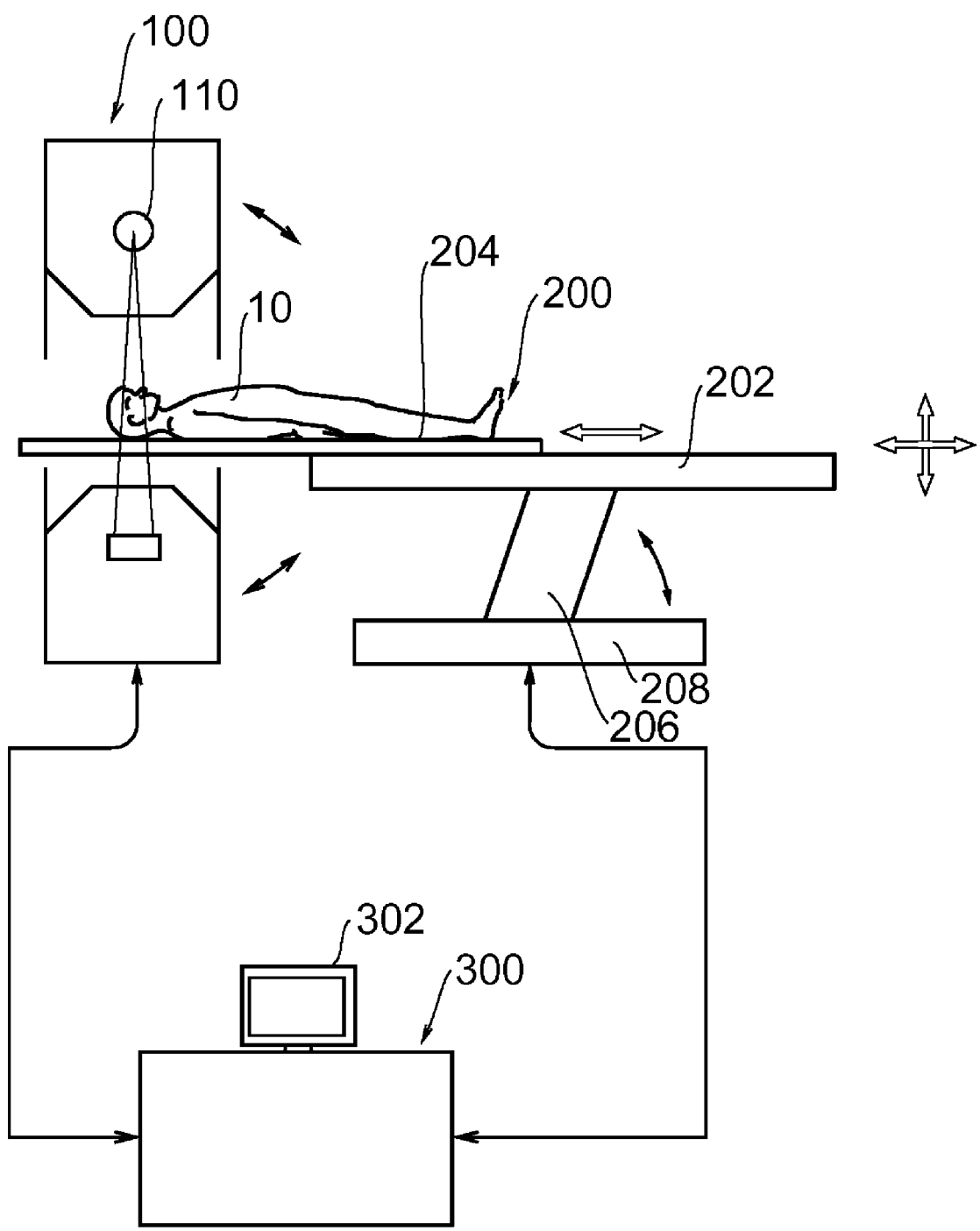
FIG. 1 is a diagram showing a configuration of an exemplary X-ray CT apparatus.

As shown in FIG. 1, this apparatus has a gantry 100, a table 200 and an operator console 300. The gantry 100 scans with an X-ray irradiating/detecting device 110 a subject 10 carried in by the table 200 to collect projected data in plural views and to input them to the operator console 300.

The operator console 300 carries out image reconstruction on the basis of the projected data inputted from the gantry 100, and displays the reconstructed image on a display 302. The image reconstruction is accomplished with a dedicated computer in the operator 300. The operator 300 is an example of image reconstructing device according to the invention.

The operator console 300 also controls the operations of the gantry 100 and the table 200. The control is accomplished by the dedicated computer in the operator 300. Under the control of the operator console 300, the gantry 100 performs a scan under prescribed scanning conditions, and the table 200 so positions the subject 10 that a prescribed region can be scanned. The positioning is accomplished by causing a built-in position adjusting mechanism to adjust the height of a table top 202 and the horizontal traveling distance of a cradle 204 on the table top.

By performing a scan in a state in which the cradle 204 is at halt, an axial scan can be accomplished. By performing a plurality of consecutive scans while moving the cradle 204 continuously, a helical scan can be accomplished. By performing a scan at every halt position while moving the cradle 204 intermittently, a cluster scan can be accomplished.

The adjustment of the height of the table top 202 is carried out by swinging a support 206 around its portion fitted to a base 208. The swinging of the support 206 displaces the table top 202 in the vertical direction and the horizontal direction. The cradle 204 travels in the horizontal direction over the table top 202 to cancel the displacement of the table top 202 in the horizontal direction. Depending on scanning conditions, a scan is accomplished in a state in which the gantry 100 is tilted. Tilting of the gantry 100 is accomplished with a built-in tilting mechanism.

Figure 2:
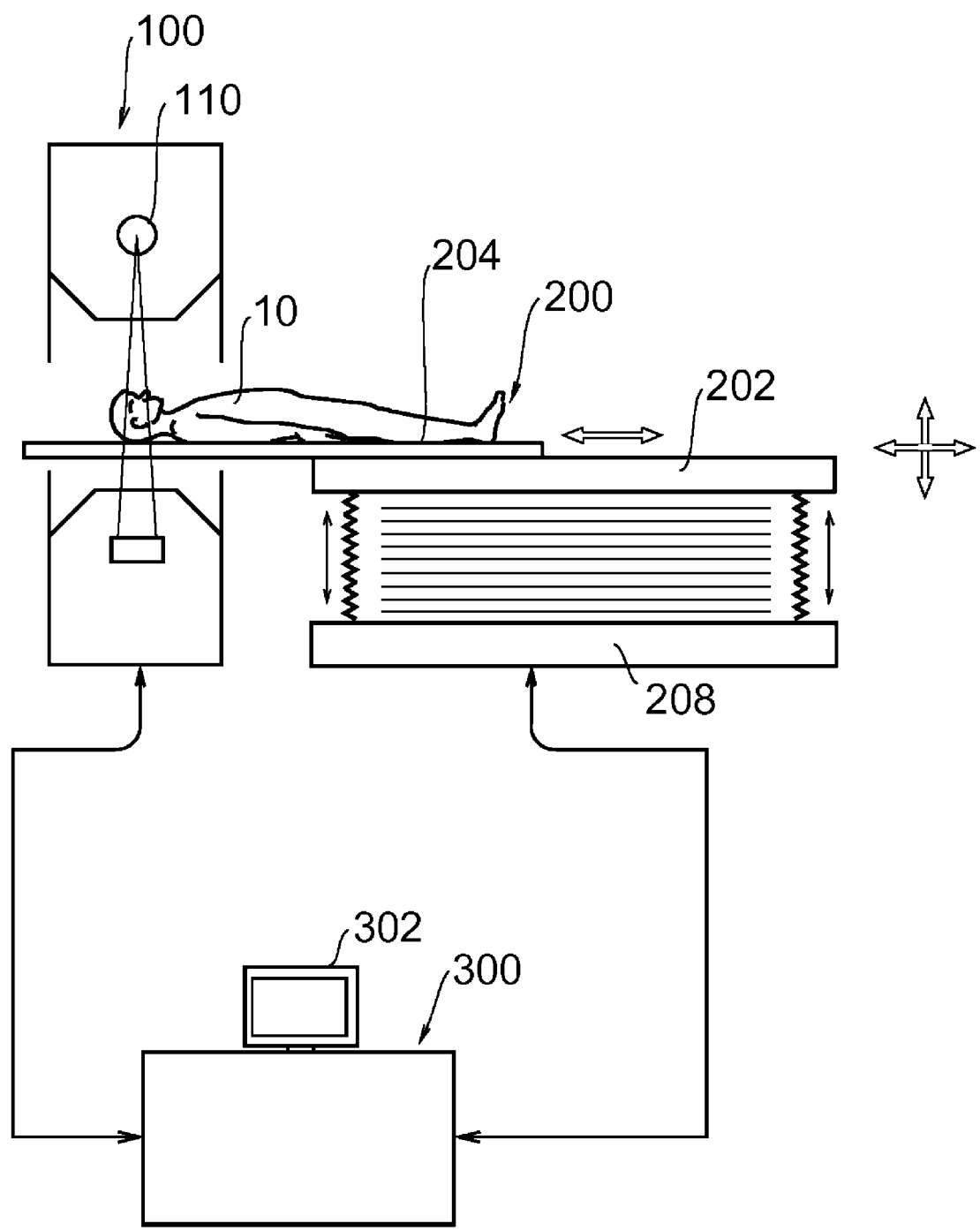
FIG. 2 is a diagram showing a configuration of another exemplary X-ray CT apparatus.

Incidentally, the table 200 may as well be of a type according to which the table top 202 moves up and down relative to the base 208 as shown in FIG. 2. The table top 202 is moved up and down by a built-in raising/lowering mechanism. In this table 200, no horizontal movement accompanies the upward or downward motion of the table top 202.

Figure 3:
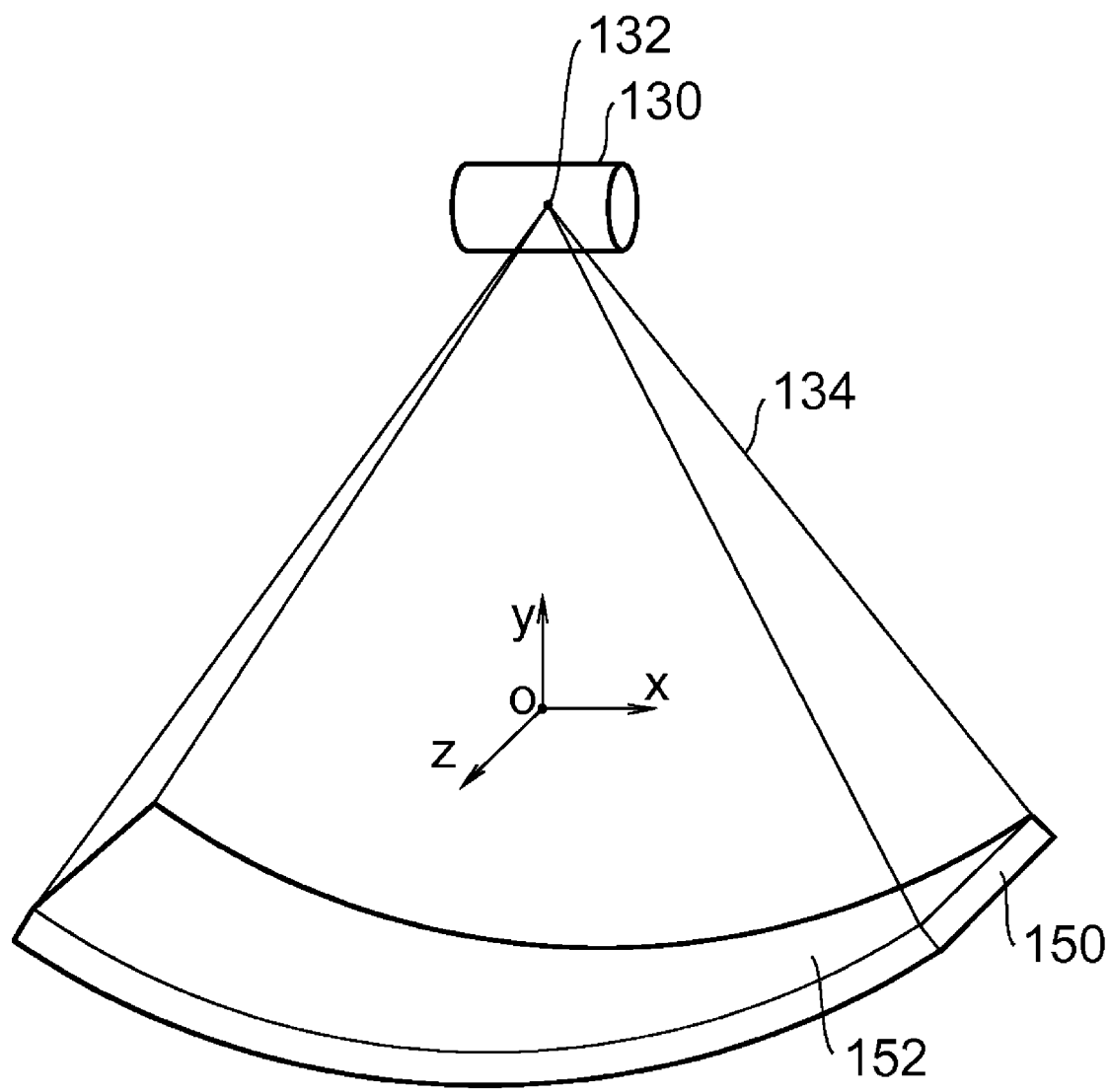
FIG. 3 is a diagram showing a configuration of an exemplary X-ray irradiating/detecting device that may be used with the X-ray CT apparatuses shown in FIGS. 1 and 2.

FIG. 3 schematically shows the configuration of the X-ray irradiating/detecting device 110. The X-ray irradiating/detecting device 110 detects with an X-ray detector 150 X-rays 134 radiated from the focus 132 of an X-ray tube 130.

The X-rays 134 are shaped by a collimator not shown into X-rays of a cone beam or a fan beam. The X-ray detector 150 has an X-ray incidence face 152 which two-dimensionally expands correspondingly to the expansion of X-rays. The X-ray incidence face 152 is so curved as to constitute a part of a cylinder. The center axis of the cylinder passes the focus 132.

The X-ray irradiating/detecting device 110 rotates around a center axis which passes the center of image pick-up, namely the isocenter O. The center axis is parallel to the center axis of the partial cylinder formed by the X-ray detector 150.

The direction of the center axis of rotation is referred to as the z direction, the direction linking the isocenter O and the focus 132 is referred to as the y direction, and the direction perpendicular to the z and y directions is referred to as the x direction. These x, y and z axes constitute the three axes of a rotational coordinate system with the z axis being as the center axis.

Figure 4:
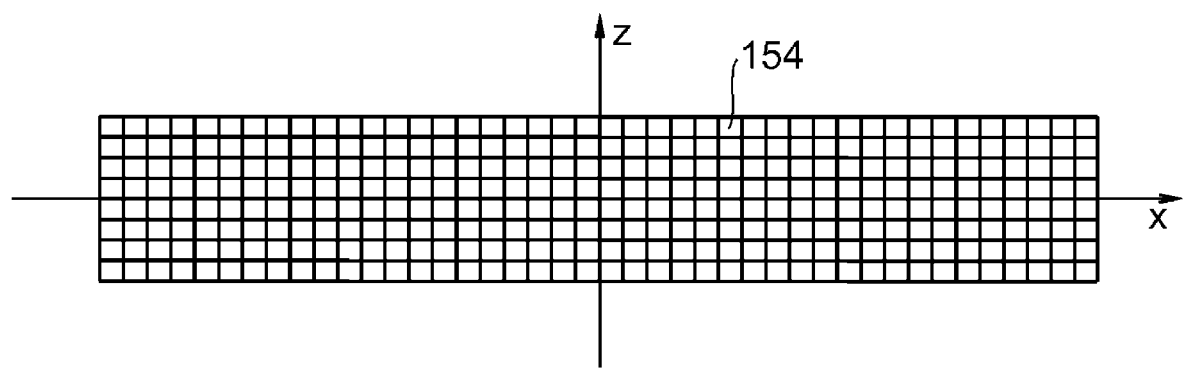
FIG. 4 is a diagram showing a configuration of an X-ray incidence face of the X-ray detector shown in FIG. 3.

FIG. 4 schematically shows a plan of the X-ray incidence face 152 of the X-ray detector 150. The X-ray incidence face 152 is formed of detection cells 154 arranged two-dimensionally in the x direction and the z direction. Thus, the X-ray incidence face 152 is a two-dimensional array of the detection cells 154. Incidentally, where X-rays of a fan beam are used, the X-ray incidence face 152 may as well be regarded as a one-dimensional array of the detection cells 154.

Each individual detection cell 154 constitutes a detection channel of the X-ray detector 150. Accordingly, the X-ray detector 150 is a multi-channel X-ray detector. The detection cell 154 is configured of a semiconductor having electrodes on both faces. As the semiconductor, CZT (cadmium zinc telluride) is used for instance. Incidentally, this is not the only option, but CdTe (cadmium telluride) or HgI2 (mercuric iodide) may as well be used. By using such a semiconductor, photons can be efficiently converted into electrical signals.

Figure 5:
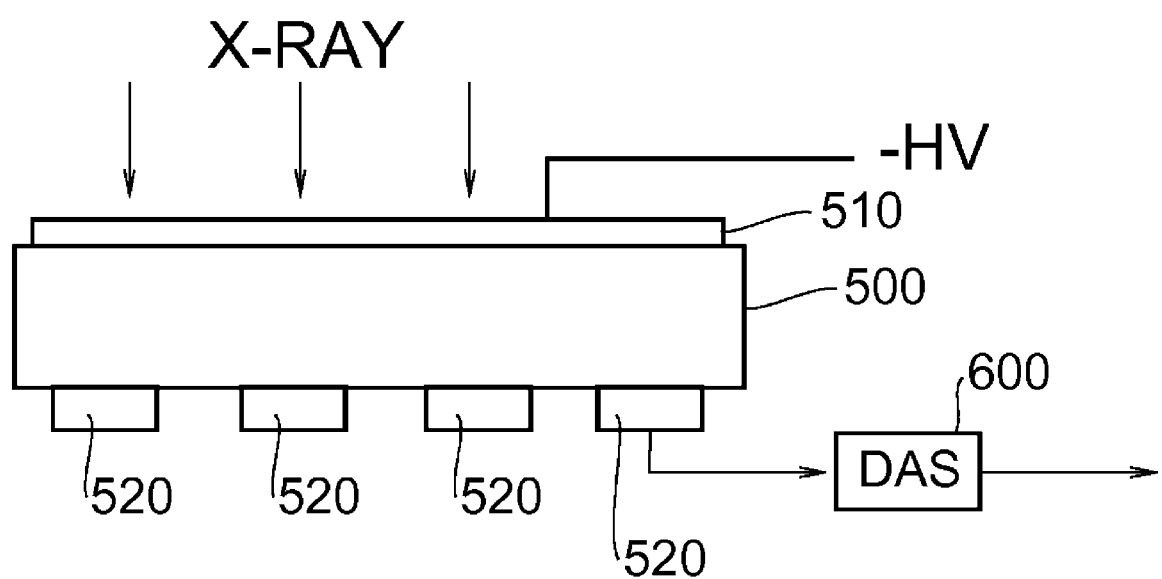
FIG. 5 is a diagram showing a configuration of another exemplary X-ray detector that may be used with the X-ray CT apparatuses shown in FIGS. 1 and 2.

FIG. 5 schematically shows one configuration of the X-ray detector 150.

As shown in FIG. 5, the X-ray detector 150 has a semiconductor substrate 500. The semiconductor substrate 500 has an electrode 510 on the face (the upper face) on which X-rays come incident. The electrode 510 is provided continuously all over the upper face. The electrode 510 constitutes a common electrode. Hereinafter, the electrode 510 may also be referred to as the common electrode. A negative high voltage −HV is applied to the common electrode 510. Incidentally, the voltage to be applied may as well be a positive high voltage +HV.

The semiconductor substrate 500 has a plurality of electrodes 520 on the side (the lower face) opposite to the X-ray incidence face. The plural electrodes 520 are two-dimensionally arranged at a prescribed pitch all over the lower face. Each of the plural electrodes 520 constitutes an individual electrode. Hereinafter, each of the electrodes 520 may also be referred to as the individual electrode. Individual electrodes 520 correspond to individual detection cells 154. Individual electrodes 520 also correspond to individual pixels.

To each of the detection cells, a DAS (data acquisition system) 600 is connected. Whereas a DAS 600 is provided for every detection cell, representative illustration will be made of only one detection cell. The DAS 600 collects data for each detection cell.

Figure 6:
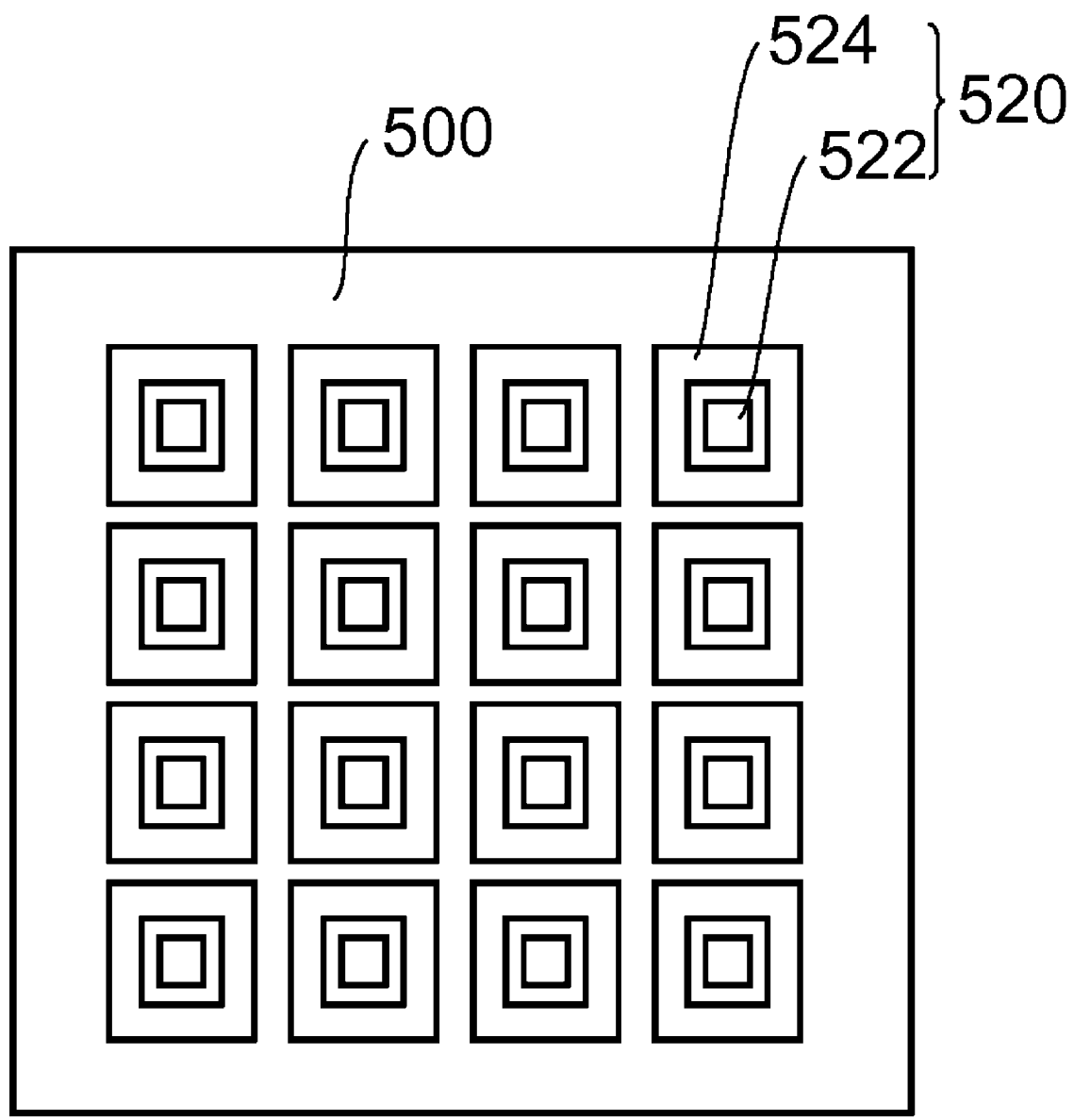
FIG. 6 is a diagram showing an electrode configuration of the X-ray detector shown in FIG. 5.

FIG. 6 shows an example of configuration of the individual electrodes 520. As shown in FIG. 6, every one of the plurality of individual electrodes 520 is configured of two electrodes 522 and 524. This results in sharing of one pixel by the electrodes 522 and 524. Incidentally, marking of reference signs on the plurality of individual electrodes and the two electrodes constituting each of them is done only in one position each to represent all the rest. The same applies hereinafter.

The relationship between the two electrodes is such that one electrode 522 is surrounded by the other electrode 524 in a complete ring shape. This arrangement facilitates distinguishing of the two electrodes. Also, the complete surrounding of one electrode enables a closed loop to be formed by the outer electrode.

Figure 7:
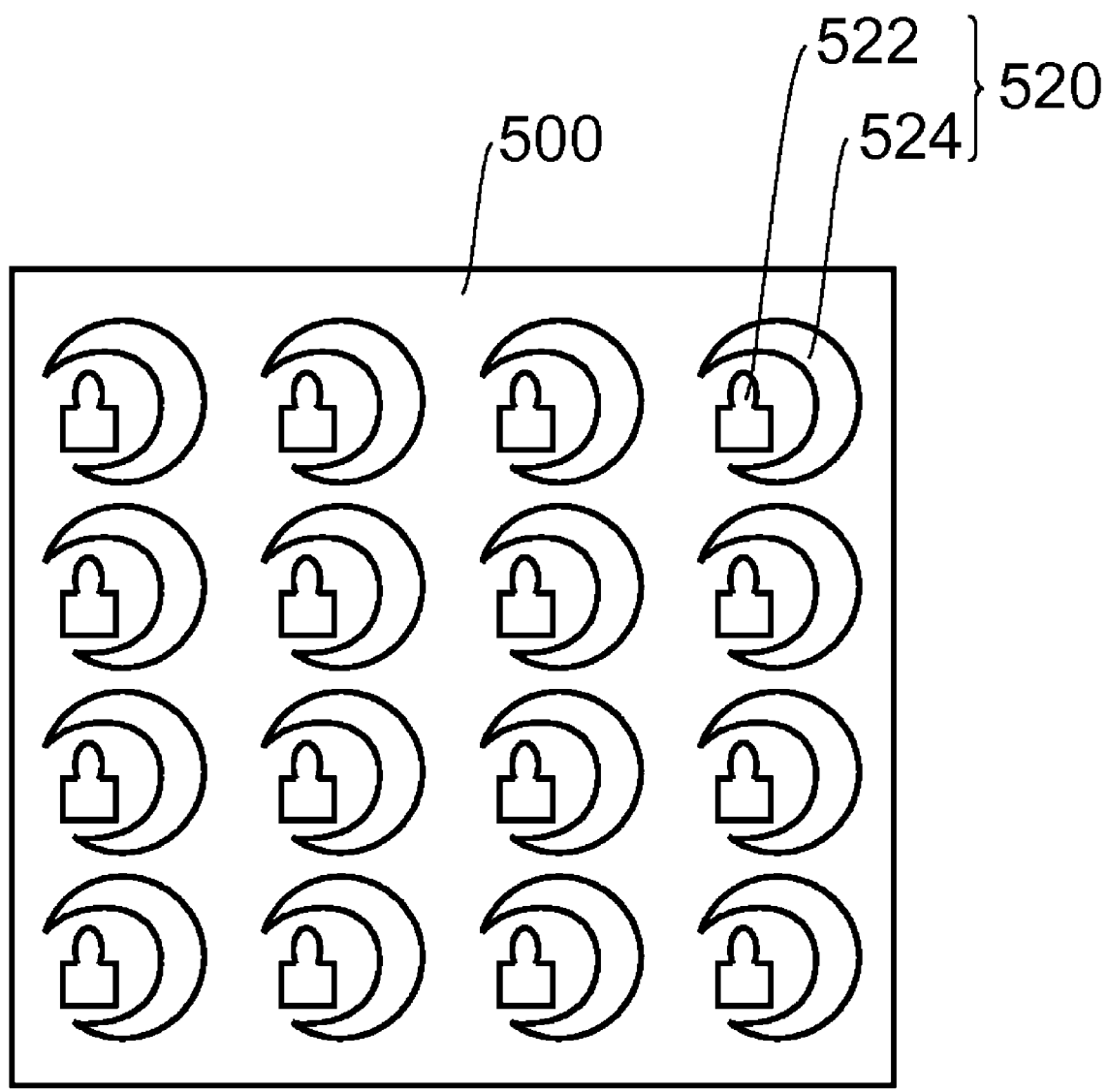
FIG. 7 is a diagram showing another electrode configuration of the X-ray detector shown in FIG. 5.
Figure 8:
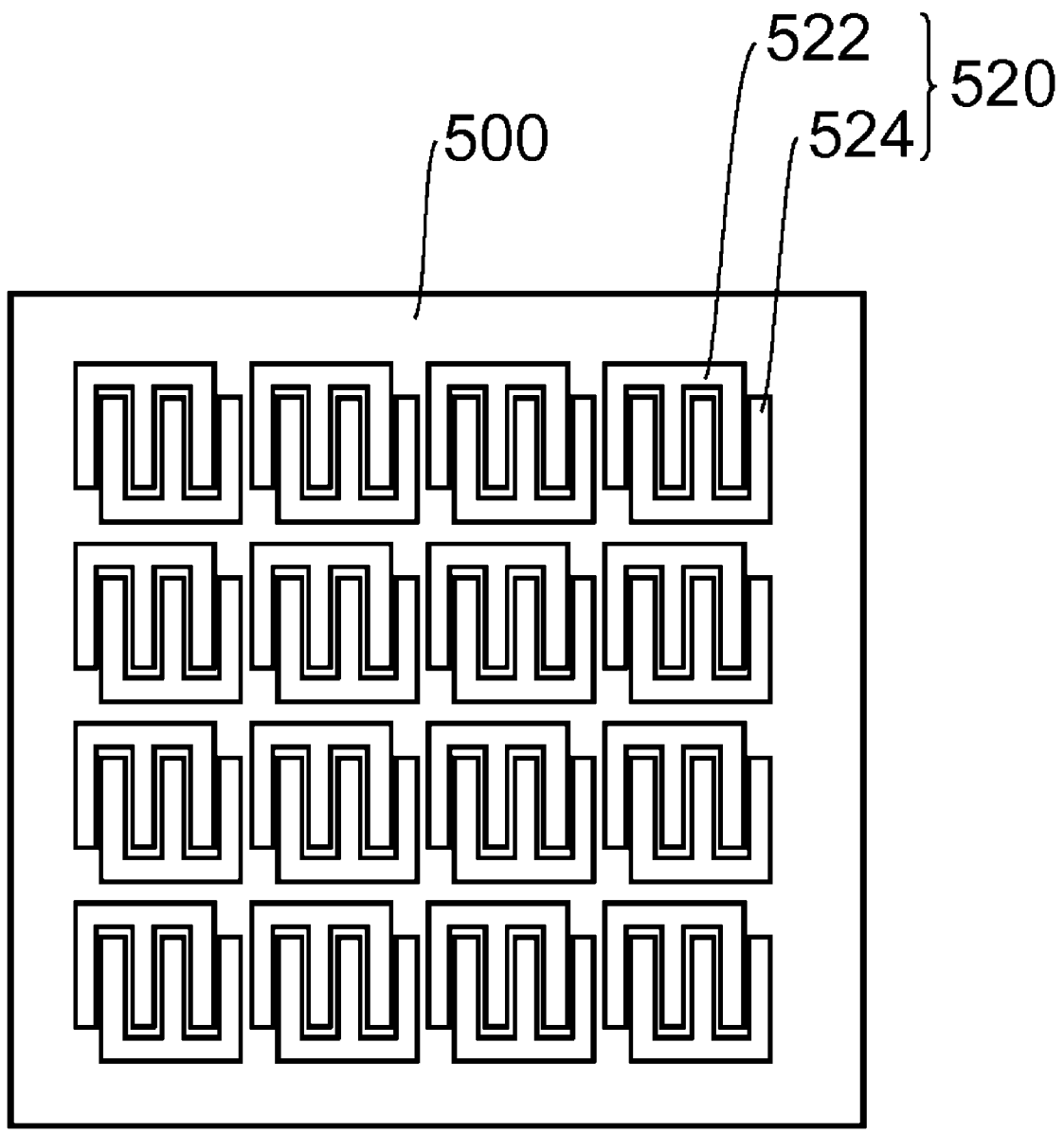
FIG. 8 is a diagram showing the electrode configuration of the X-ray detector.

Incidentally, the relationship between the two electrodes 522 and 524 is not limited to this, but one electrode 522 may as well be surrounded by the other electrode 524 in an incomplete ring shape as shown in FIG. 7 or one electrode 522 and the other electrode 524 alternately engage with each other in a combined comb shape as shown in FIG. 8. Incomplete surrounding of electrodes facilitates taking out signals from the inner electrode, or the relationship of alternate engagement serves to improve the equality between the two electrodes. Various other ways of combination are also conceivable. The electrode 522 is one example of individual electrodes of the first group according to the invention. The electrode 524 is one example of individual electrodes of the second group according to the invention.

Figure 9:
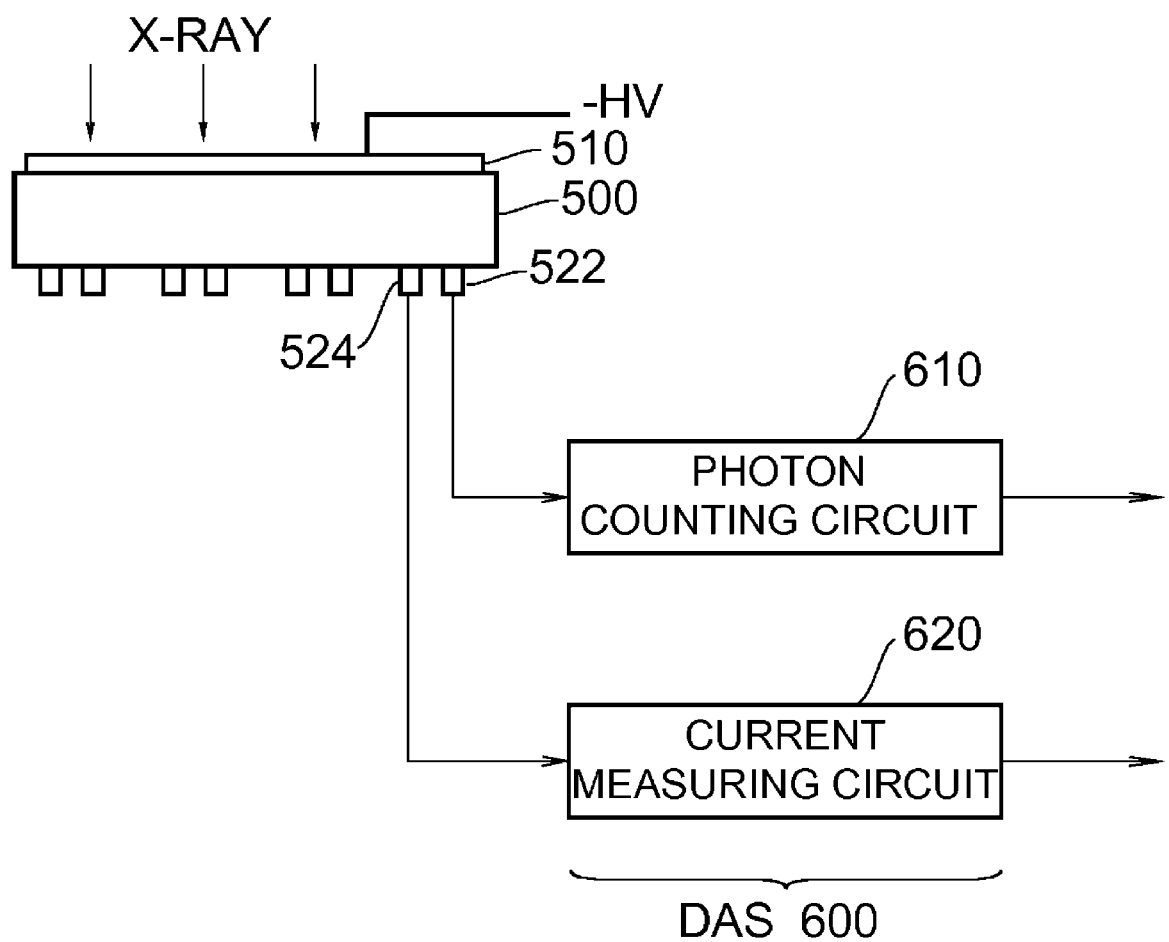
FIG. 9 is a diagram showing the relationship between electrodes and a DAS.

FIG. 9 shows the relationship between the two electrodes 522 and 524 and the DAS 600 with respect to one detection cell. The relationship similarly applies to all the other detection cells. As shown in FIG. 9, the electrode 522 is connected to the photon counting circuit 610 of the DAS 600. The photon counting circuit 610 counts input signals from the electrode 522 in the photon counting mode. This causes the number of photons of X-rays to be counted. The flux rate that can be addressed in the photon counting mode can be altered by varying the size of the electrode 522.

The counting is accomplished by distinguishing the energy of the photons. The distinguishing of the energy is carried out on the basis of a prescribed threshold. By setting a plurality of thresholds, a plurality of energies can be distinguished. Incidentally, the photons can as well be counted without distinguishing the energy. The photon counting circuit 610 is one example of first data collecting device according to the present invention.

The electrode 524 is connected to the current measuring circuit 620 of the DAS 600. The current measuring circuit 620 measures input signals from the electrode 524 in the current measuring mode. This results in measuring of the signal intensity of X-rays. Unlike the photon count, the input current is not saturated even if the flux rate of the X-rays becomes high. The current measuring circuit 620 is one example of second data collecting device according to the invention.

Figure 10:
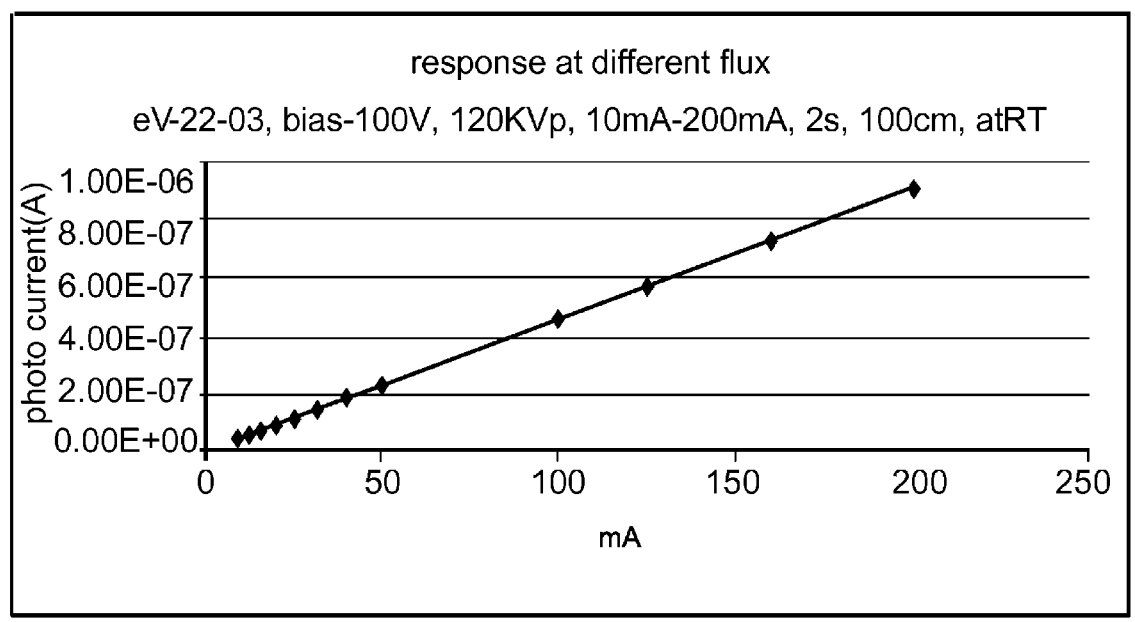
FIG. 10 is a diagram showing the results of measurement of the input current.
Figure 11:
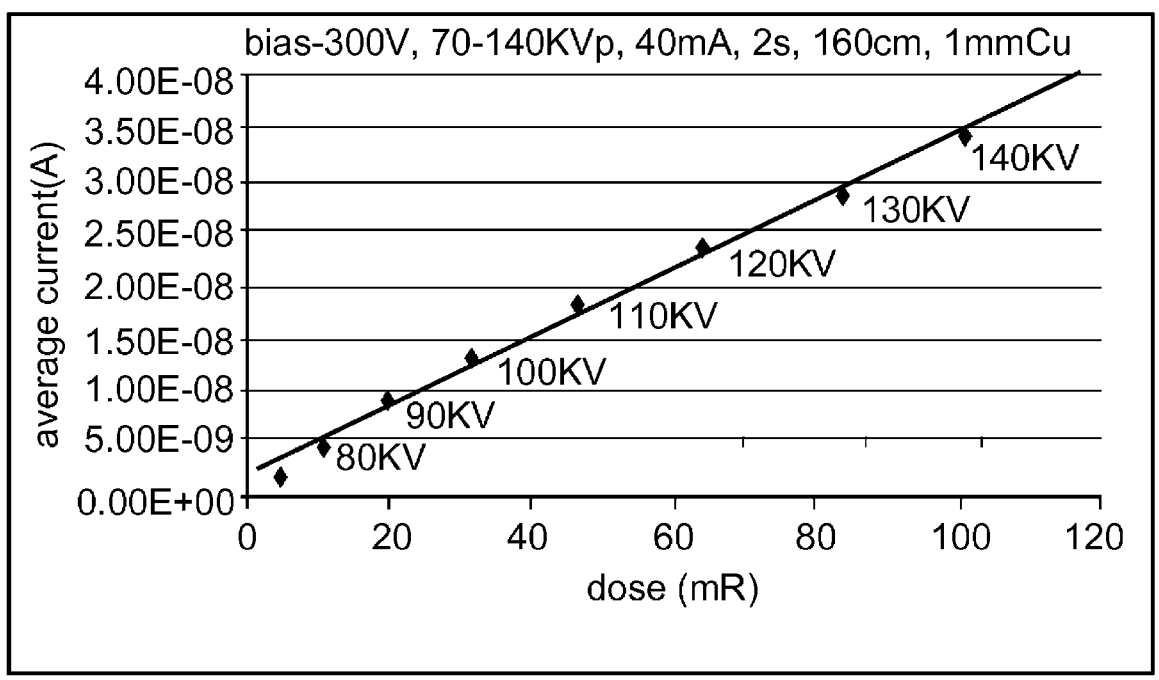
FIG. 11 is a diagram showing the results of measurement of the input current.
Figure 12:
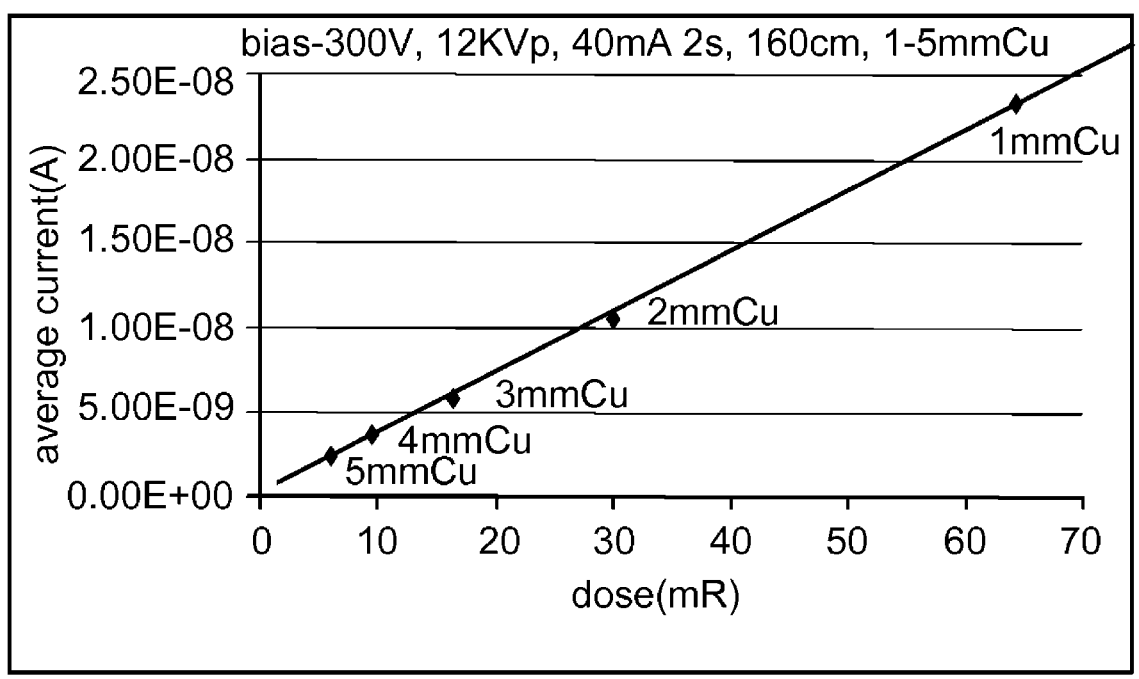
FIG. 12 is a diagram showing the results of measurement of the input current.

Graphs of the results of actual measurement of the input current are shown in FIG. 10 through FIG. 13. FIG. 10 shows variations in the input current when the tube current (shown along the y-axis) of the X-ray tube (shown along the x-axis) is varied. Any increase in the tube current corresponds to an increase in the flux rate of the X-rays. FIG. 11 shows variations in the input current (shown along the y-axis) when the tube voltage (shown along the x-axis) of the X-ray tube is varied. Any increase in the tube voltage corresponds to an increase in the flux rate. FIG. 12 shows variations in the input current when the thickness of a copper plate located between the X-ray tube and the X-ray detector is varied. Any decrease in the absorption count corresponds to an increase in the flux rate of the X-rays. It is evident from these graphs that the input current linearly increases without saturation with a rise in the flux rate of the X-rays.

Figure 13:
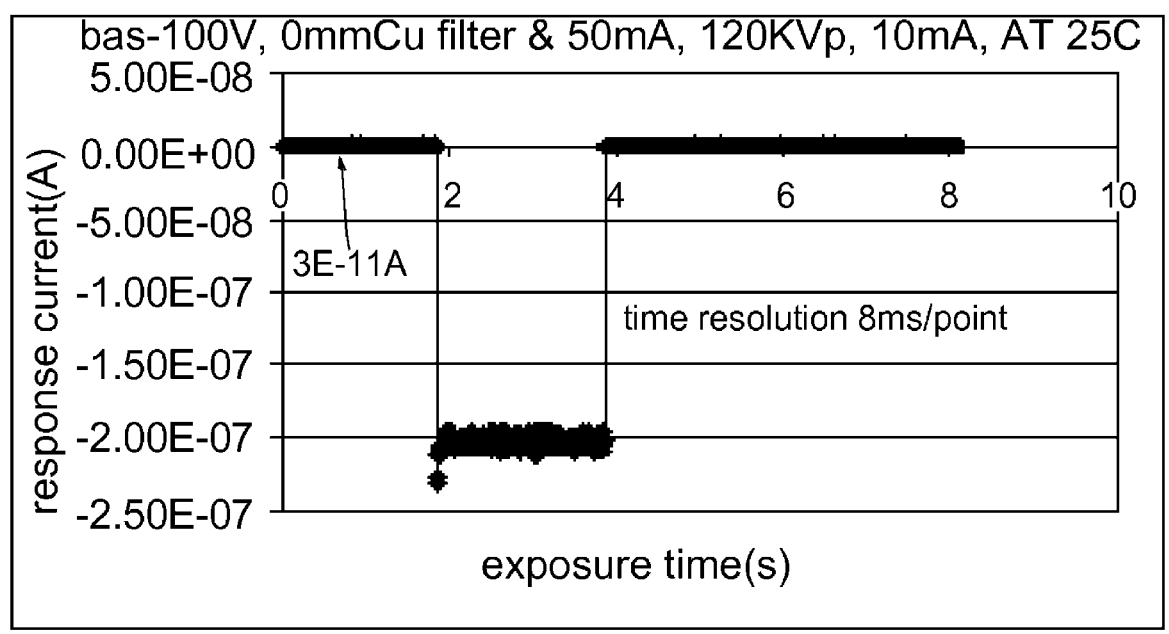
FIG. 13 is a diagram showing the results of measurement of the input current.

FIG. 13 shows variations in the input current when the absorption count is increased stepwise to return to its original level. It is evident from this graph that no hysteresis occurs from any increase or decrease in absorption count.

This makes the X-ray detector 150 adaptable to low to high flux rates with the single-layered semiconductor substrate 500. In this X-ray detector 150, the size of the detection cells 154, namely the pixel size, can be readily set to about 0.1 mm. Therefore, an X-ray detector which is excellent in space resolving power can be easily obtained. Moreover, as it has only a single detection layer, its manufacturing cost is far lower than that of a multi-layered product.

Images are respectively reconstructed from the count of the photon counting circuit 610 and the measurement of the current measuring circuit 620. The reconstructed image based on the photon count gives a tomogram representing the distribution of a specific element in a part of the object 10 where a large quantity of X-rays is absorbed. When a plurality of thresholds are used at the time of photon counting, a tomogram in which a plurality of element are individually distinguished is obtained. On the other hand, the reconstructed image based on the measured current gives a tomogram representing the distribution of X-ray absorption coefficients in the object 10.

Figure 14:
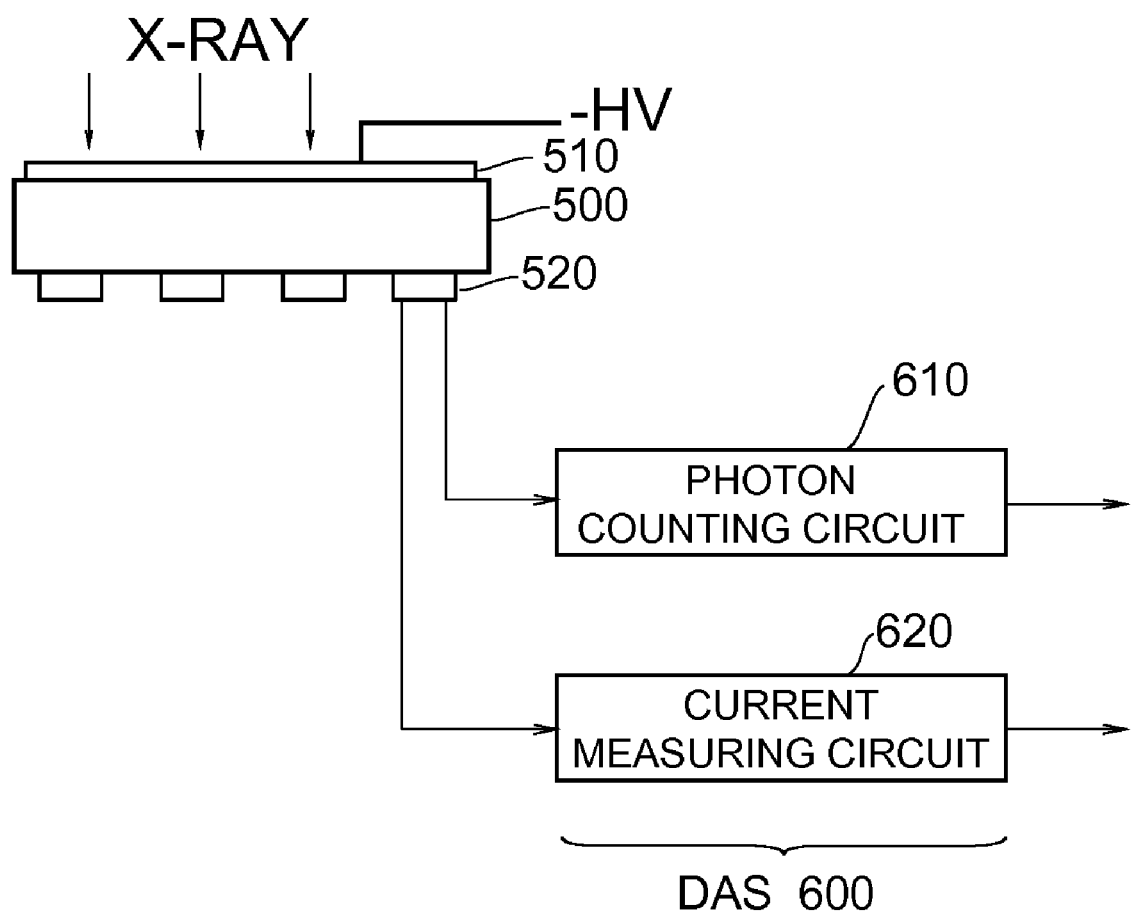
FIG. 14 is a diagram showing a configuration of another exemplary X-ray detector that may be used with the X-ray CT apparatuses shown in FIGS. 1 and 2.

The two electrodes of each detection cell may be integrated as the electrode 520 as shown in FIG. 14, and from the electrode 520, signals are inputted to each of the photon counting circuit 610 and the current measuring circuit 620. In this way, too, photon counting and current measuring can be accomplished of the same pixels by the photon counting circuit 610 and the current measuring circuit 620, respectively.

Figure 15:
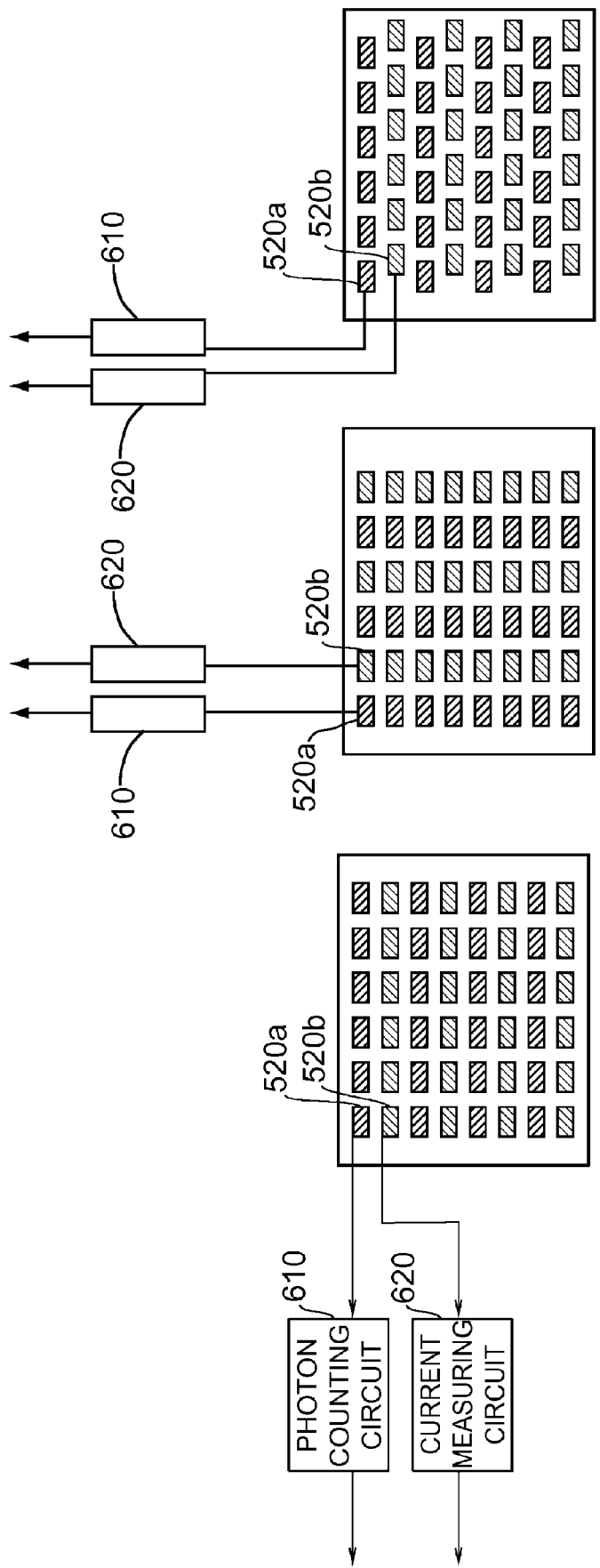
FIGS. 15(a) to 15(c) are diagrams each showing an electrode configuration of the X-ray detector shown in FIG. 14.

Photon counting by the photon counting circuit 610 and current measuring by the current measuring circuit 620 may as well be accomplished of different pixels. Such a case is shown in FIGS. 15(a) to (c). As shown in FIGS. 15(a) to (c), the photon counting circuit 610 is connected to an electrode 520a, and the current measuring circuit 620 is connected to an electrode 520b.

The electrode 520a and the electrode 520b are the electrodes of different detection cells, and are alternately arranged over the semiconductor substrate 500. The alternate arrangement of the electrode 520a and the electrode 520b may be a longitudinal alternate arrangement as shown in FIG. 15(a), a lateral alternate arrangement as shown in FIG. 15(b) or an alternate arrangement with half-pitch lags as shown in FIG. 15(c). Incidentally, the electrode 520a and the electrode 520b may as well be alternately arranged in both longitudinal and lateral directions.

Figure 16:
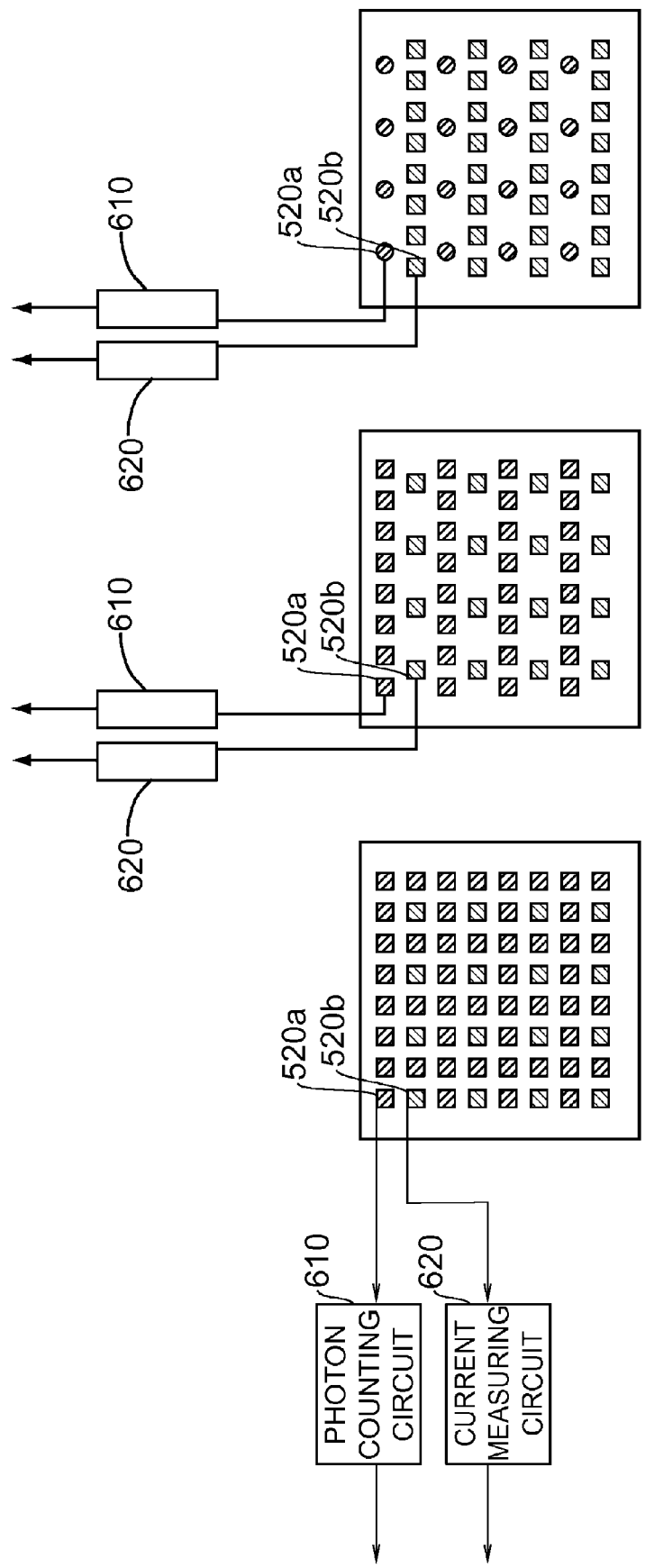
FIGS. 16(a) to 16(c) are diagrams each showing an electrode configuration of the X-ray detector shown in FIG. 14.

The electrodes 520a and the electrodes 520b, as shown in FIGS. 16(a) to 16(c), may as well be differentiated in distribution density over the semiconductor substrate 500. FIG. 16(a) shows an alternate arrangement in the longitudinal direction of rows in which all are electrodes 520a and rows in which electrodes 520a and electrodes 520b alternate each other; FIG. 16(b), an alternate arrangement in the longitudinal direction of rows of electrodes 520a in high density and electrodes 520b in low density; and FIG. 16(c), an alternate arrangement in the longitudinal direction of rows of electrodes 520a in low density and electrodes 520b in high density. Incidentally, the electrodes 520a and the electrodes 520b may differ in shape and/or size.

Figure 17:
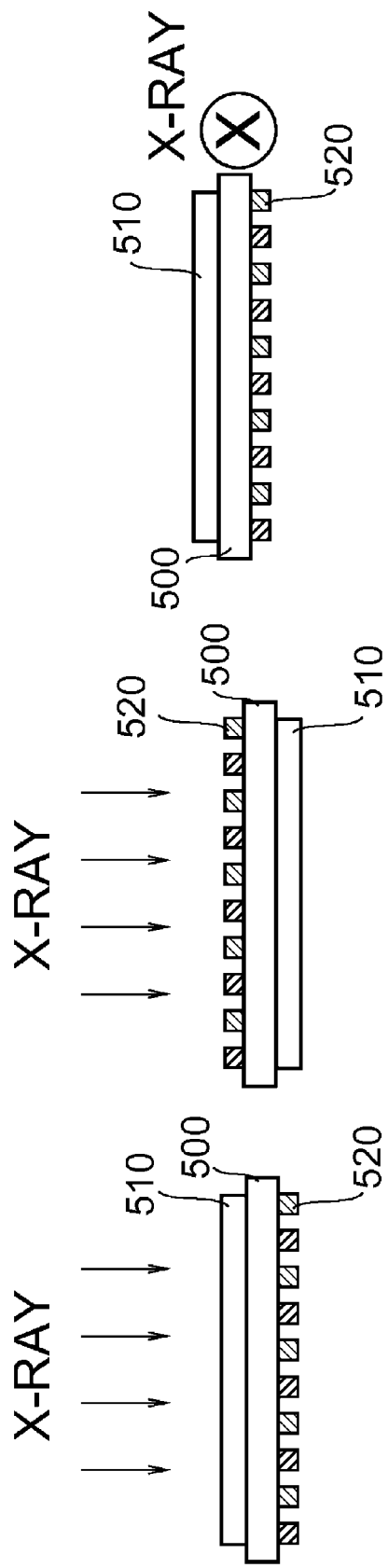
FIGS. 17(a) to 17(c) are diagrams each showing the incident direction of X-rays.

The semiconductor substrate 500 having such detection cells is used with its common electrode side facing the incident direction of X-rays as shown in FIG. 17(a); its individual electrode side facing the incident direction of X-rays as shown in FIG. 17(b); or the semiconductor layer between the common electrodes and the individual electrodes facing the incident direction of X-rays as shown in FIG. 17(c). Its use in this way makes it adaptable to the one-dimensional distribution of X-rays.

Figures 18A, 18B:
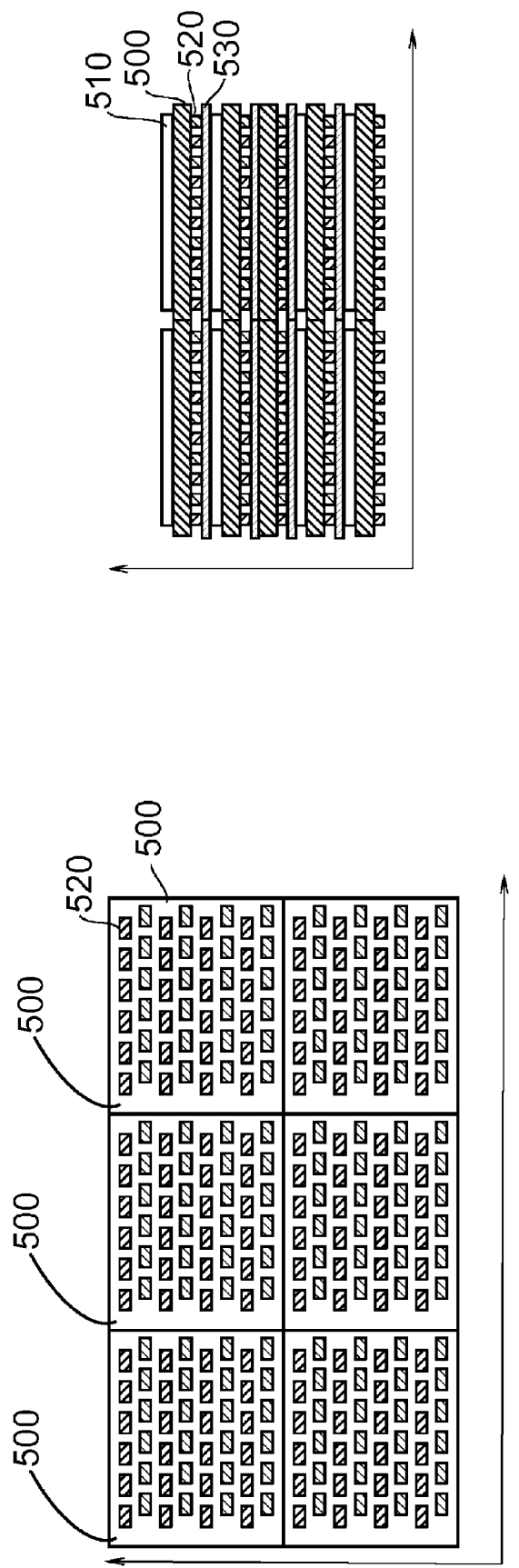
FIGS. 18(a) and 18(b) are diagrams each showing a combination of a plurality of semiconductor substrates.

When the common electrodes or the individual electrodes are to be oriented in the incident direction of X-rays, a plurality of semiconductor substrates 500 are arranged in the same plane as shown in FIG. 18(a). On the other hand, when a side face of the semiconductor layer between the common electrodes and the individual electrodes is to be oriented in the incident direction of X-rays, layers are stacked with an insulating layer placed in-between in the thickness direction as shown in FIG. 18(b). In this way, adaptation to the two-dimensional extension of cone beam X-rays can be achieved.

The X-ray detector 150 can also detect other radiations than X-rays. Therefore, by injecting a radioactive tracer into the object 10 and scanning the object without irradiating him or her with X-rays, it is possible to obtain projected data resulting from the counting of photons radiated from the tracer.

By performing image reconstruction on the basis of such projected data, the distribution of the tracer in the object 10 can be visualized. Thus, this apparatus can also operate as a SPECT (single photon emission computed tomography) apparatus.

The X-ray CT apparatus is not limited to an X-ray CT apparatus for medical use, but may as well be an X-ray CT apparatus for industrial use or the like. Scanning can also be accomplished by turning the object without turning the X-ray irradiating/detecting apparatus. Or the X-ray irradiating/detecting apparatus and the object may as well be turned in reverse directions to each other.

What is claimed is:

1. An X-ray detector comprising:
   a single-layered semiconductor substrate comprising an array of detection cells configured to directly convert photons of X-rays into electrical signals;
   a first data collecting device configured to collect data with respect to said array of detection cells in a photon counting mode; and
   a second data collecting device configured to collect data with respect to said array of detection cells in a current measuring mode.

2. The X-ray detector according to claim 1, wherein:
   said first and second data collecting devices are each configured to collect data regarding common detection cells of said array of detection cells.

3. The X-ray detector according to claim 1, wherein:
   said first and second data collecting devices are each configured to collect data regarding different detection cells of said array of detection cells.

4. The X-ray detector according to claim 2, wherein:
   said array of detection cells comprises:
   a common electrode arranged on one of a front face and a rear face of said semiconductor substrate; and
   a plurality of individual electrodes arranged on the other of said front face and said rear face of said semiconductor substrate.

5. The X-ray detector according to claim 4, wherein:
   said plurality of individual electrodes comprises a first group of individual electrodes for said first data collecting device, and a second group of individual electrodes for said second data collecting device.

6. The X-ray detector according to claim 5, wherein:
   said first group of individual electrodes and said second group of individual electrodes share pixels.

7. The X-ray detector according to claim 5, wherein:
   said first group of individual electrodes and said second group of individual electrodes do not share pixels.

8. The X-ray detector according to claim 4, wherein:
   said array of detection cells undergo:
   incidence of X-rays on said common electrode side of said semiconductor substrate.

9. The X-ray detector according to claim 4, wherein:
   said array of detection cells undergo:
   incidence of X-rays on said individual electrode side of said semiconductor substrate.

10. The X-ray detector according to claim 4, wherein:
    said array of detection cells undergo:
    incidence of X-rays on a side face of a semiconductor layer positioned between said individual electrodes and said common electrode.

11. An X-ray CT apparatus comprising:
    a single-layered semiconductor substrate comprising an array of detection cells configured to directly convert photons of X-rays into electrical signals;
    a first data collecting device configured to collect data with respect to said array of detection cells in a photon counting mode;
    a second data collecting device configured to collect data with respect to said array of detection cells in a current measuring mode; and
    an image reconstructing device configured to reconstruct a first image based on the data collected by said first data collecting device and a second image based on the data collected by said second data collecting device.

12. The X-ray CT apparatus according to claim 11, wherein:
    said first and second data collecting devices are each configured to collect data regarding common detection cells of said array of detection cells.

13. The X-ray CT apparatus according to claim 11, wherein:
    said first and second data collecting devices are each configured to collect data regarding different detection cells of said array of detection cells.

14. The X-ray CT apparatus according to claim 11, wherein:
    said array of detection cells comprises:
    a common electrode arranged on one of a front face and a rear face of said semiconductor substrate; and
    a plurality of individual electrodes arranged on the other of said front face and said rear face of said semiconductor substrate.

15. The X-ray CT apparatus according to claim 14, wherein:
    said plurality of individual electrodes comprises a first group of individual electrodes for said first data collecting device, and a second group of individual electrodes for said second data collecting device.

16. The X-ray CT apparatus according to claim 15, wherein:
    said first group of individual electrodes and said second group of individual electrodes share pixels.

17. The X-ray CT apparatus according to claim 15, wherein:
    said first group of individual electrodes and said second group of individual electrodes do not share pixels.

18. The X-ray CT apparatus according to claim 14, wherein:
    said array of detection cells undergo:
    incidence of X-rays on said common electrode side of said semiconductor substrate.

19. The X-ray CT apparatus according to claim 14, wherein:
    said array of detection cells undergo:
    incidence of X-rays on said individual electrode side of said semiconductor substrate.

20. The X-ray CT apparatus according to claim 14, wherein:
    said array of detection cells undergo:
    incidence of X-rays on a side face of a semiconductor layer positioned between said individual electrodes and said common electrode.

* * * * *